US009022258B2

(12) United States Patent
Nehren et al.

(10) Patent No.: US 9,022,258 B2
(45) Date of Patent: May 5, 2015

(54) MULTI-COMPONENT MIXING SYSTEM HAVING A ROTATABLE CONTAINER AND CONTAINER THEREFOR

(75) Inventors: Klaus-Dieter Nehren, Dormagen (DE); Andreas Grundler, Dormagen (DE); Udo Friese, Hagen (DE); Susanne Botzum, Hanau (DE); Manuel Meier-Staude, Germering (DE); Guenter Jasper, Cologne (DE); Uwe Lanzendorf-Linkweiler, Dormagen (DE); Heike Hennen, Huerth (DE); Alf Memmer, Ratingen (DE); Michael Freckmann, Cologne (DE)

(73) Assignee: Heraeus Kulzer GmbH, Hanau (DE)

( * ) Notice: Subject to any disclaimer, the term of this patent is extended or adjusted under 35 U.S.C. 154(b) by 0 days.

(21) Appl. No.: 13/825,240

(22) PCT Filed: Sep. 13, 2011

(86) PCT No.: PCT/EP2011/004590
§ 371 (c)(1),
(2), (4) Date: Mar. 20, 2013

(87) PCT Pub. No.: WO2012/038038
PCT Pub. Date: Mar. 29, 2012

(65) Prior Publication Data
US 2013/0181012 A1 Jul. 18, 2013

(30) Foreign Application Priority Data

Sep. 21, 2010 (DE) .......................... 10 2010 045 935

(51) Int. Cl.
*B29B 7/80* (2006.01)
*A61C 9/00* (2006.01)
(Continued)

(52) U.S. Cl.
CPC ........... *A61C 9/0026* (2013.01); *B01F 13/1055* (2013.01); *B01F 15/0237* (2013.01); *B65D 83/0011* (2013.01); *B65D 83/0027* (2013.01); *B29B 7/80* (2013.01)

(58) Field of Classification Search
CPC .................. B65D 83/0027; B65D 83/0011
USPC ............................ 222/390, 1, 333, 167, 135, 222/145.5–145.7; 366/162.1
See application file for complete search history.

(56) References Cited

U.S. PATENT DOCUMENTS 3,241,729 A * 3/1966 Gabler .......................... 222/390
3,325,063 A * 6/1967 Hansen ......................... 222/390
(Continued)

FOREIGN PATENT DOCUMENTS

CH        623535 A5      6/1981
DE        492413 C       2/1930
(Continued)

OTHER PUBLICATIONS

Int'l Search Report and Written Opinion issued Jan. 18, 2012 in Int'l Application No. PCT/EP2011/004590.
(Continued)

*Primary Examiner* — Donnell Long
(74) *Attorney, Agent, or Firm* — Panitch Schwarze Belisario & Nadel LLP (57) ABSTRACT

A container (10, 30, 50) is provided for single- or multi-component molding materials. The container has a container body (12, 32, 52) having a constant outer contour in a longitudinal extent of the container (10, 30, 50), a piston (17, 37) movable in the longitudinal direction, and a cover (11, 31) having an outlet opening (13, 33, 53). A volume for a molding material is defined between the piston (17, 37) and the cover (11, 31), the volume being variable in the direction of the longitudinal extent of the container (10, 30, 50). The container distinguishes itself in that the container body (12, 32, 52) is rotatable relative to the outlet opening (13, 33, 53), and the piston (17, 37) thereby pushes out the content of the container (10, 30, 50).

12 Claims, 4 Drawing Sheets

(51) Int. Cl.
*B01F 13/10* (2006.01)
*B01F 15/02* (2006.01)
*B65D 83/00* (2006.01)

(56) References Cited

U.S. PATENT DOCUMENTS

| | | | |
|---|---|---|---|
| 3,432,078 A * | 3/1969 | Hall | 222/80 |
| 4,429,811 A * | 2/1984 | Bakeman | 222/159 |
| 5,054,657 A * | 10/1991 | Morse et al. | 222/162 |
| 6,012,610 A | 1/2000 | Pauser et al. | |
| 6,311,869 B1 | 11/2001 | Horth et al. | |
| 6,619,508 B2 * | 9/2003 | Balcome et al. | 222/136 |
| 6,837,612 B2 | 1/2005 | Bublewitz et al. | |
| 6,957,747 B2 * | 10/2005 | Peeler et al. | 222/1 |
| 7,325,707 B2 * | 2/2008 | Bougamont et al. | 222/390 |
| 7,467,734 B2 * | 12/2008 | Bocola | 222/390 |
| 8,029,204 B2 * | 10/2011 | deVirag et al. | 401/75 |
| 8,079,499 B2 * | 12/2011 | Juteau et al. | 222/390 |
| 8,590,747 B2 * | 11/2013 | Keller | 222/137 |
| 8,627,987 B2 * | 1/2014 | Pollack et al. | 222/405 |
| 2008/0056061 A1 | 3/2008 | Pauser et al. | |
| 2008/0317544 A1* | 12/2008 | Spirk et al. | 401/277 |
| 2009/0140007 A1* | 6/2009 | Voss | 222/135 |
| 2013/0020350 A1* | 1/2013 | Gardos et al. | 222/1 |

FOREIGN PATENT DOCUMENTS

| | | |
|---|---|---|
| DE | 3615691 A1 | 11/1987 |
| DE | 19618718 A1 | 11/1997 |
| DE | 10038882 A1 | 4/2001 |
| DE | 19951504 A1 | 5/2001 |
| DE | 10112904 A1 | 10/2002 |
| DE | 10164385 C1 | 3/2003 |
| DE | 102010013750 A1 | 7/2011 |
| EP | 0787655 A1 | 8/1997 |
| EP | 1836992 A1 | 9/2007 |
| GB | 2193944 A * | 2/1988 |
| WO | 2010081205 A2 | 7/2010 |

OTHER PUBLICATIONS

Office Action issued Apr. 14, 2011 in DE Application No. 10 2010 045 935.6.

Office Action issued Jul. 2, 2012 in DE Application No. 10 2010 045 935.6.

Office Action issued Feb. 7, 2014 in DE Application No. 10 2010 045 935.6.

* cited by examiner

MULTI-COMPONENT MIXING SYSTEM HAVING A ROTATABLE CONTAINER AND CONTAINER THEREFOR

CROSS-REFERENCE TO RELATED APPLICATIONS

This application is a Section 371 of International Application No. PCT/EP2011/004590, filed Sep. 13, 2011, which was published in the German language on Mar. 29, 2012, under International Publication No. WO 2012/038038 A1 and the disclosure of which is incorporated herein by reference.

BACKGROUND OF THE INVENTION

The invention relates to a container for single-component or multi-component molding materials, comprising a container body having a constant outer contour in a longitudinal extent of the container, a piston movable in the longitudinal direction, and a cover having an outlet opening, wherein a volume provided for a molding material is defined between the piston and the cover, the volume being variable in the direction of the longitudinal extent of the container. The invention also relates to a container system for multi-component molding materials having at least two such containers, a method for applying a mass from such a container, and a method for mixing multiple masses from such containers with such a container system using such a method.

Molding materials, especially molding materials for dental purposes, are used to produce, by molding or casting, a negative mold of an area of the body, for example a jaw or teeth, wherein this mold is then filled with a suitable material, such as gypsum (plaster of Paris), to form a positive mold of the molded area. In this way, a copy of the cast mold, called a "model," is produced. Such models are used to produce, for example, defect prostheses or teeth replacements. They can also be used for diagnoses or treatment planning.

Because the molding mass or material must be separated from the molded object in a non-destructive way, it must be a material that solidifies relatively slowly and has an at least limited elastic or elastomeric property. Because the material must also be true to the drawing, in order to oppose a change of its surface shape with as little resistance as possible during the molding and in order to be able to transfer the assumed shape as exactly as possible to the model, suitable molding materials are usually those that are subjected to a chemical or physical change after the molding or even during the molding. Suitable molding materials are, among others, alginate, hydrocolloid, silicone, polyether, gypsum, or wax.

Here, multi-component materials are sometimes used that are stored separately from each other, for example as a base paste and as a catalyst paste, and for use are mixed together in a certain mixing ratio, for example in a ratio of five parts base paste to one part catalyst paste.

The viscous base paste and catalyst paste are stored either in cans or tubes and mixed by hand or stored in tube-bag systems or multiple-chamber cartridges and dosed by hand-driven or motor-driven devices, conveyed, and simultaneously mixed by static or rotating attachments.

For completely filling molding ladles, motor-driven devices are being used more and more, which are equipped with 360 ml to 380 ml double cartridges or tube bags. These container sizes are sufficient for ten ladle fillings, on average. Therefore, these devices are used with replaceable, rotating mixing attachments provided for one-time use. Because the mixing ratios of the base paste and catalyst paste are fixed, the devices have a common conveying feed for both components, so that the preparation time cannot be varied by the user, in which, for example, more or less catalyst paste is added relative to the base paste.

In dental practice, mixing devices have become known, for example according to European Patent EP 0 492 413 B1, which feed their reactive components in a fixed mixing ratio from double cartridges, such as according to German published patent application DE 100 38 882 A1, or double tube-bag combinations, such as according to European patent application publication EP 0 787 655 A1, and homogenize these components into mixtures by dynamic mixing attachments, such as from German Patent DE 101 64 385 C1 or German published patent application DE 101 12 904 A1, which are cross-linked to form elastomeric molding materials. The mixing ratio of the two components is here specified in currently common devices by the cross sections of the respective component container, since both components are fed with the same piston speed for discharging the container contents.

In German published patent application DE 199 51 504 A1, a mixing device is described, which can be equipped with at least two different components, in order to control the properties of the reactive mixture by a control unit. The properties to be varied are here the viscosity and the bonding time of the reactive mixture. These properties are controlled by varying the mixing ratio through separate control of the individual discharge piston speeds. In this way, an individual mixture composition can be generated from multiple different stored components. Thus, for example, in addition to the otherwise typical base and catalyst components, a viscosity component and a catalyst accelerating component can also be added.

From German published patent application DE 196 18 718 A1, the use of a decelerating component is known, which is not dosed continuously with the remaining components into the dynamic mixer, but instead is optionally injected in advance laterally into the mixer, in order to delay the curing of the mixing mass supplied at the beginning, since this mass would otherwise harden earlier than the rest of the supplied mass.

A dosing apparatus having a mixing device is disclosed in European patent application publication EP 1 836 992 A1. This apparatus discloses a holder for a double cartridge having two cartridges of different diameters, wherein a larger cartridge is provided for a base material and a smaller cartridge is provided for a catalyst material. The device has, for each of the cartridges, pistons that are pressed in sync into the cartridges in the direction of the outlet openings. The two cartridges are connected at their outlets to a mixing device having an input for each of the two cartridges. This mixing device is driven by a driveshaft that runs between the two cartridges. When the material is applied, the pistons are retracted again, so that a new double cartridge can be introduced. This dosing apparatus according to EP 1 836 992 A1 is at least twice as long as the cartridges, since in the retracted position of the pistons, the piston rods for both cartridges are arranged within the apparatus.

Force-fit connections between the drives or motors and the shafts to be driven on dynamic mixing attachments or even a screw piston drive are typically produced by hexagonal connectors. In EP 1 836 992 A1 other forms of these connections are also set forth. There, it is also described that insertion of the connection parts is made simpler.

One problem of these rigid connections is that under pressure strong stresses occur on the shafts and seals due to deformation of multiple parts of the entire system. As a result, higher friction losses occur, which significantly increase the drive energy to be applied for mixing or feeding or lead to leaks at sealing surfaces. In addition, the molding materials in the described system are preferably highly viscous, wherein their viscosity lies in the range of viscous honey to modeling clay, and thus large amounts of force must be transmitted from the drive to the piston, in order to press the material from an outlet opening. Due to the large forces occurring, the parts must have a very stable construction, which increases the material consumption, the weight, and the costs. On the other hand, the containers are susceptible to failure or can even be completely destroyed during operation.

Another disadvantage is that the replacement of the containers is time intensive due to the construction, since the drive must be connected to the shaft in a force-fit manner. Finally, it cannot be seen for the produced mixture whether the correct mixing ratio was used.

BRIEF SUMMARY OF THE INVENTION

Starting from this prior art, the present invention is based on the object of providing a container and a container system for multi-component molding materials and also providing a method, which overcome the disadvantages of the prior art. In particular, the container and thus the container system must have a more stable construction and therefore must be less susceptible to failure. In addition, the containers must be easy to replace and the specified mixing ratio must be constant during the discharge of the different pastes.

This object is achieved in that, in the interior of the container, a thread is arranged that engages in a counter thread of the piston and the piston is rotatably mounted relative to the thread. The container body is rotatably mounted relative to the outlet opening, and a rotation of the container body relative to the outlet opening leads to a rotation of the piston relative to the thread, such that the variable volume can be varied.

Such a container, which could be a cartridge in the scope of the invention, can be driven from the outside on the periphery of the container body. The molding mass is located in the variable volume of the container, where it can be arranged, in particular, in a suitable tube bag or can be filled in the volume without a bag.

The containers according to the invention are replaceable, without a drive shaft having to be completely retracted into a dosing device and without the drive having to be inserted in a force-fit manner into a small opening of a drive shaft, so that a reduced time effort for replacing a container results. For multi-component systems individual containers that are already exhausted can also be replaced without having to replace the other containers that could perhaps still hold material.

In a container according to the invention, it can be provided that the cover is arranged on the end of the container opposite in the original position of the piston, wherein the original position of the piston is that at which the variable volume is at a maximum.

The original position is understood to be the position in which the container is filled, thus in which a paste is stored in the variable volume and can be driven from the container.

It can also be provided that the container body is rotatably mounted relative to the cover having the outlet opening and a rotation of the container body relative to the cover leads to a movement of the piston in the container, whereby the variable volume can be varied.

It can be further provided that a fastener is arranged on the cover or the outlet opening for fastening the container to a discharge device, a mixer, or a handle.

It is also advantageous if the cover and/or the outlet opening is connected tightly to the container body.

Containers according to the invention can also be distinguished in that a connection for a drive, in particular a belt pulley, a rubberized periphery, or a ring gear, is arranged on the outside of the container body.

One embodiment of the invention provides that the thread is an external thread, which is arranged on a spindle arranged in the interior of the container and fixed to the cover or is constructed as an internal thread on the inner walls of the container body.

One embodiment of the invention provides that the container body has a cylindrical shape and the piston has a circular cross section, wherein the thread is arranged as an internal thread on the inner side of the container body and the counter thread is arranged as an external thread on the outer side of the piston and wherein the piston includes an opening, through which at least one rod and/or one tube extends in the longitudinal direction of the container, wherein this rod and/or tube is or are connected to the outlet opening and/or the cover, so that the piston cannot rotate relative to the outlet opening.

Here, it can be provided that the rod or the rods have a non-round cross section, in particular a polygonal cross section, preferably a hexagonal cross section.

An alternative embodiment of the invention provides that, in the center in the interior of the container in the direction of the longitudinal extent there is a spindle comprising the thread as an external thread, wherein the spindle is connected rigidly to the outlet opening and/or to the cover, and wherein the piston comprises a central opening having the counter thread as an internal thread, through which the spindle extends, wherein the piston is movable in the longitudinal direction relative to the container body, but is not rotatably mounted relative to the container body and is sealed tightly with the inner walls of the container body.

Here, it can be provided that the container body and the piston have non-round cross sections, wherein the container body and the piston are, in particular, oval, polygonal, or round cornered, especially preferred hexagonal.

The object is also achieved by a container system for multi-component molding materials having at least two containers according to the invention, wherein a container is provided for each component of the molding material, the outlet openings and/or the covers of the container are detachably connected to each other, in particular pluggable, wherein the container bodies are rotatably mounted independently from each other.

Here, it can be provided that all of the container bodies are rotatably mounted relative to the container system via belts, gears, rollers, or toothed belts by at least one drive, preferably each by a motor, especially preferred independently from each other.

Furthermore, it can be provided that multiple drives are provided for multiple container bodies, wherein the rotational speeds of the container bodies can be specified and/or set independently of each other or in constant ratios, and for this purpose a control element is preferably provided for the input of parameters.

One advantageous embodiment of the container system is realized if multiple drives are provided for multiple container bodies, wherein the rotational speeds for the drive shafts of the different container bodies can be specified or set independently of each other or in constant ratios. Here, the ratios themselves are also adjustable. Thus, the user can preset, for example, whether he wants a mixing ratio of 4:1, 5:1, or 6:1 for a certain mixture of base material and catalyst material.

The invention is also achieved by a method for applying a paste-like mass from a container according to the invention, wherein the container body is rotated relative to the outlet opening, so that the piston is moved by the thread in the direction of the cover and the content of the container is pressed out through the outlet opening.

According to the invention, a method is also provided for mixing multiple masses from containers according to the invention with a container system according to the invention, wherein a method according to the invention is used and the rotational speeds of the container bodies are set as a function of a desired mixing ratio.

The invention is based on the surprising recognition that, through the external drive on the cartridge, the force transmission is performed on one hand with a large lever (torque) and at the same time the surface area of the force transmission is especially large compared with a more direct drive of the spindle, and thus the design has less wear. Therefore, the force for the drive can be transmitted in a significantly easier way and a more reliable propulsion of the piston is achieved that is less susceptible to failure.

In addition, such a container can also be replaced more easily, because the drive can be connected more loosely and more easily to the outer side of the container body, for example by rollers that can be enveloped with a rubber material. Such a simple connection of the container body to the drive also achieves a sufficient force transmission to create a more reliable propulsion of the piston, due to the radius of the container body which acts as a lever.

Another advantage results if the containers of a container system all have the same diameter. Then, it can be immediately recognized, namely using the rotational speeds of the different containers, which mixing ratio was just generated. By suitable colored marking of the outer walls of the container bodies, the visual effect here can be amplified.

A screw-like piston movement can be generated, for example, in the following way: if the screw thread is located on the drive shaft/spindle, then the piston can be prevented from rotating, in that the piston outer side and container inner walls have guide grooves and guide springs or the cross sections of the containers are oval or round cornered. It is also possible to drive any piston with more than one spindle shaft or to guide additional guide rods through the piston in addition to the spindle shaft. In this way, the piston is screwed forward on the rotating spindle shaft.

Alternatively, the containers could have a circular cross section. The drive shaft and piston are connected to each other with force fit, e.g. by a square, hexagon, or the like, and the piston rotates at the same time. Here, the outer side of the piston and the inner side of the container walls have threads that are matched to each other. Therefore, the piston screws itself in the container.

By round-cornered container cross sections, in which the material outlet ports sit in the rounded corners of end plates, three or more component containers can also be positioned close to each other in the device. This allows the docking of a mixing attachment without retraction.

In cases where the material outlet ports are closed with a seal or membrane, it is possible to open the container in the device by piercing, which is advantageous in terms of handling and time compared with other typical screw or plug caps.

In this way, because each individual container can assume an individual piston position and has its own piston drive, the control of various material parameters of the molding material mixture is possible by variation of the mixture ratios. By the arrangement of the piston rods in the component container, the device size can be significantly reduced or the storage capacity of consumable material in the devices can be increased, without the devices having to be even larger than before.

The variation of the consistency of the mixing material can be realized by storing two or more consistency-defining base components in the containers. One of these base components here represents the greatest desired consistency, while the other base component represents the lowest consistency.

In ISO 4823, "Elastomeric molding materials," these consistencies are divided into type classes. The greatest consistency is here the type 0, which is designated as moldable. The lowest consistency is type 3, which is designated as easy-flowing.

By varying the percentage ratios of the base components type 0 and type 3, all other consistencies lying between the extremes, such as type 1, poorly flowing, and type 2, average flowing, can be set continuously or in steps. Preferably, however, the consistencies are limited to only type 0 to type 2, because type 3 is almost always used in distinctly smaller quantities and is typically added by a hand mixing device directly onto the patient. For the use of consistencies in the entire range from type 0 to type 3, at least one other base component would also be necessary, because the molding materials of type 3 have not only a lower consistency than the other materials, but typically also deviate from the other types in terms of properties, such as Shore hardness, scanability, hydrophilicity.

Another universal component, which is added for forming the elastomers by chemical reaction, is stored in another container in the device. This component, designated as an activator, cross-linker, or catalyst, could be added in a smaller portion of the mixture, in order to keep its influence on consistency low. By stepwise or continuous changing of the dosing ratio between the base components and the activator component, the reactivity of the mixture and thus the so-called processing time can be adapted individually to the requirements of the user. To realize this, the individual components have separate dosing drives.

It has proven especially advantageous for the ergonomic construction of the container system to drive a spindle not in the rotationally blocked piston, but instead to drive the container walls or the container bodies rotationally and to block the spindle from rotating. This is realized in that the head piece, which is also connected rigidly to the spindle outside an outlet opening, is locked in the device. If the container body is set into rotation, the piston also simultaneously rotates, because this rotates with the piston, for example by guide rails (groove and spring). Therefore, the piston screws itself into the container and pushes the paste located therein out of the outlet opening.

In this way, because the drive occurs via the outer walls of the container body, in this container according to the invention, the drive can sit next to the container, and thus allow a simple replacement of individual containers. Here, the other containers can remain in the container system. At the same the openings, which are also feed channels to the mixing nozzles, can have short constructions. If the drive is realized, however, by a head plate on the spindle, the distance between the container and mixing nozzle increases also. This is disadvantageous both on account of loss of material and also loss of force due to the longer throughflow channels. By reducing to a total of three necessary components consisting of two base components from whose mixture ratio the consistency is regulated, and the activator component, whose dosing quantity controls the processing time, the entire feeding mechanism can be driven by a single motor. The respective dosing ratios are here regulated by gears, which would have the advantage of reducing the device size.

Advantageously, however, instead of using a universal activator component, the preselected processing time is controlled by the ratio of two different components. These two components can be two activator components having different reactivity values. Likewise, it has also proven effective to use a combination of a catalyst component and a decelerating component (retarder, inhibitor), which can be used combined with each other according to the preselected processing time. If a combination of a catalyst/decelerator is used, the total portion of these components relative to the portion of base components can be held constant, which is advantageous for controlling the preselected consistency.

In order to be able to also maintain the preselected processing time, independent of the sometimes significantly fluctuating temperatures that occur in dentistry, the temperature of the paste mixture can be measured and taken into account.

The features, properties, and advantages mentioned for the different subjects of the invention, that is, for the container according to the invention, for the container system according to the invention, and for the method according to the invention, are applicable without restriction and in the same way also for the other subjects of the invention.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

The invention is explained below on the basis of four schematically represented drawings and described without restricting the general concept of the invention on the basis of embodiments with reference to the drawings, wherein reference is made explicitly to the drawings for all inventive details not explained in more detail in the text. In the drawings.

DETAILED DESCRIPTION OF THE INVENTION

Figure 1:
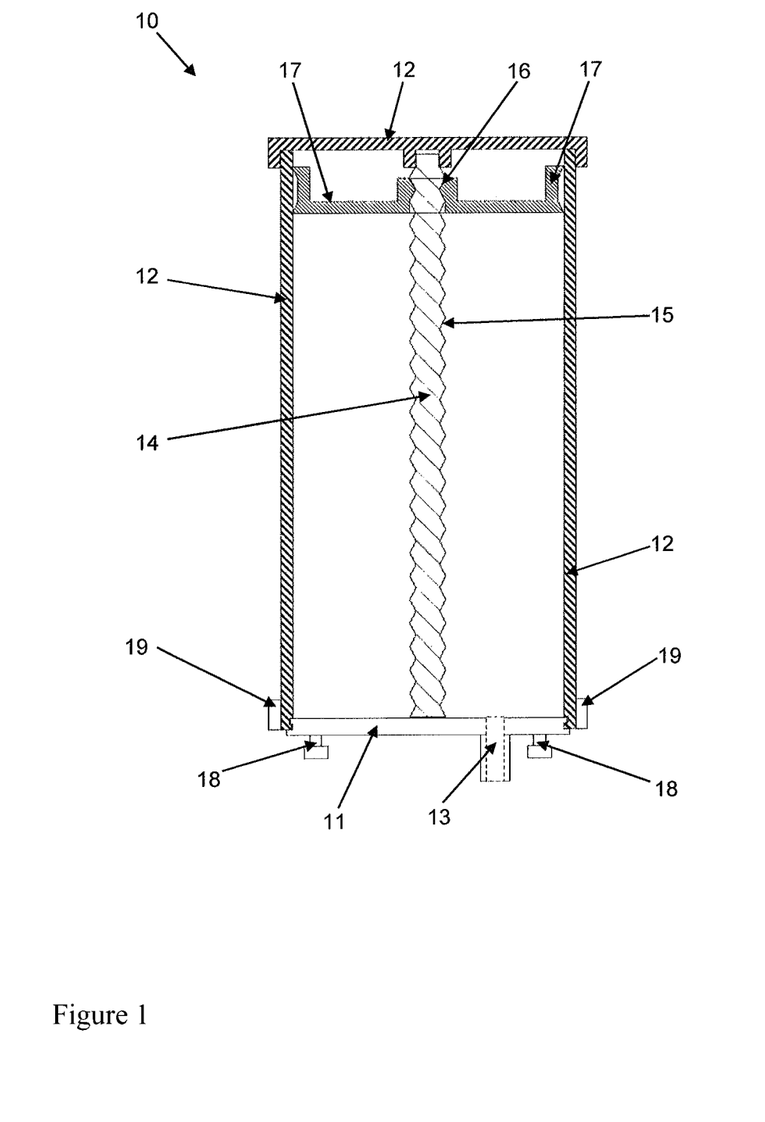
FIG. 1 is a schematic longitudinal sectional view through a container according to an embodiment of the invention.

FIG. 1 shows a schematic longitudinal section view along the longitudinal axis of a container 10 according to an embodiment of the invention. This container has a cover 11 that can be removed, in order to fill the container 10 with molding material. The container 10 comprises, in addition to the cover 11, a container body 12 that, together with the cover 11, seals the container 10 against the outside. The container body 12 is mounted relative to the cover 11 so that it can rotate about an axis running perpendicular through the cover 11. The cover 11 includes an outlet opening 13. On the side opposite the cover 11 the container 10 is closed.

A spindle 14, which acts as a drive shaft, runs centrally through the container 10, which has a tubular cross section. The spindle 14 is connected rigidly to the cover 11. The spindle 14 has a thread in the shape of an external thread 15 that interacts with a counter thread in the form of an internal thread 16 of a piston 17. The piston 17 is mounted locked against rotation in the side walls of the container body 12, for example by a non-round construction of the piston 17 and the lateral container inner walls of the container body 12, so that when the spindle 14 rotates, the piston 17 is moved in the direction of the cover 11, while reducing the variable volume between the outlet opening 13 and the piston 17.

The cover 11 is rotatably mounted relative to the side walls of the container body 12, so that a rotation of the spindle 14 exclusively about the longitudinal axis of the container 10 results. The container body 12 according to FIG. 1 can also involve an oval or rounded corner container body 12, so that a rotational movement of the piston 17 relative to the container body 12 is prevented for this reason.

A rotation of the spindle 14 thus forces a movement of the piston 17 in the direction toward the outlet opening 13. In this way, the molding material (not shown) located in the volume of the container 10 between the piston 17 and the outlet opening 13 is set under pressure and pressed out of the outlet opening 13. The container 10 is here shown in the original position in which the piston 17 is arranged on the end of the container interior opposite the cover 11, so that the volume that can be pressed out is at a maximum.

On the cover 11 there are fasteners 18 in the form of pins, with which the container 10 can be connected to a discharge device, a mixing device, or the like. These devices can be connected to the outlet opening 13.

On the outer periphery of the container body 12 there is arranged a ring gear 19 that completely surrounds the cylindrical container body 12. With this ring gear 19 the container body 12 can be rotated relative to the cover 11 and the outlet opening 13 by a driving gear or a toothed belt. The rotation leads to a rotation of the piston 17 with the container body 12. Due to the thread 14, 15, the piston 17 moves when it rotates in the counterclockwise direction (when looked at from above) in the direction of the cover 11, whereby the contents of the container 10 contained in the variable volume are pressed out through the outlet opening.

On the sides of the piston 17 facing the inner walls of the container body 12, seals are provided that should prevent the contents of the variable volume from being discharged into the upper part of the container 10 when a pressure builds up.

Figure 2:
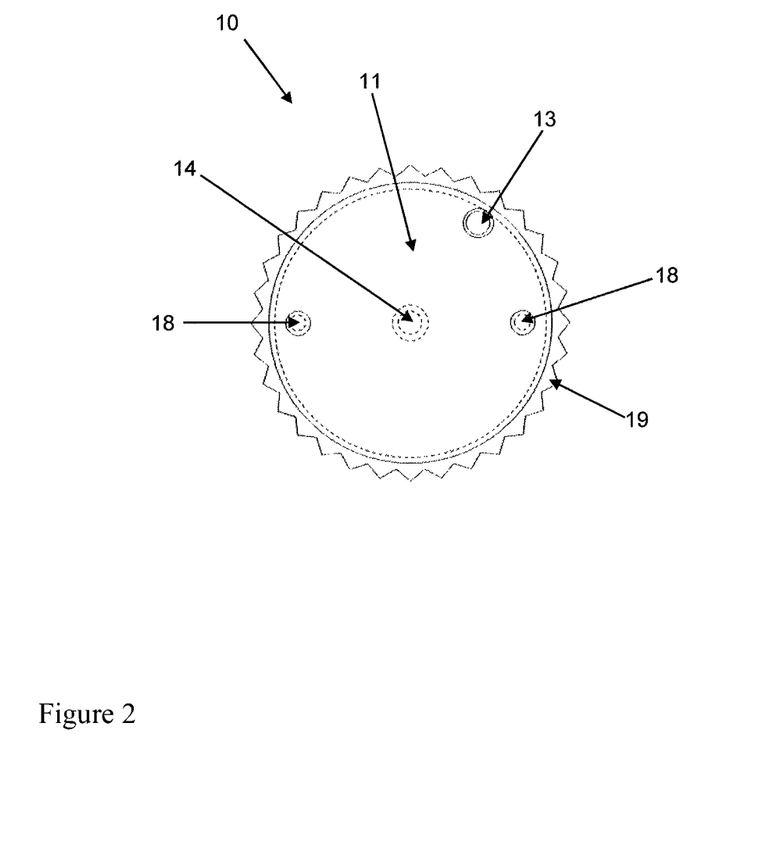
FIG. 2 is a schematic top view of a cover of the container according to the invention as per the embodiment of FIG. 1.

FIG. 2 shows a top view of the cover 11 of the container 10 according to the invention of FIG. 1. The positioning of the two fasteners 18 can be recognized therein, as well as the arrangement of the outlet opening 13 and the spindle 14. The ring gear 19 is arranged peripherally around the container body 12.

Figure 3:
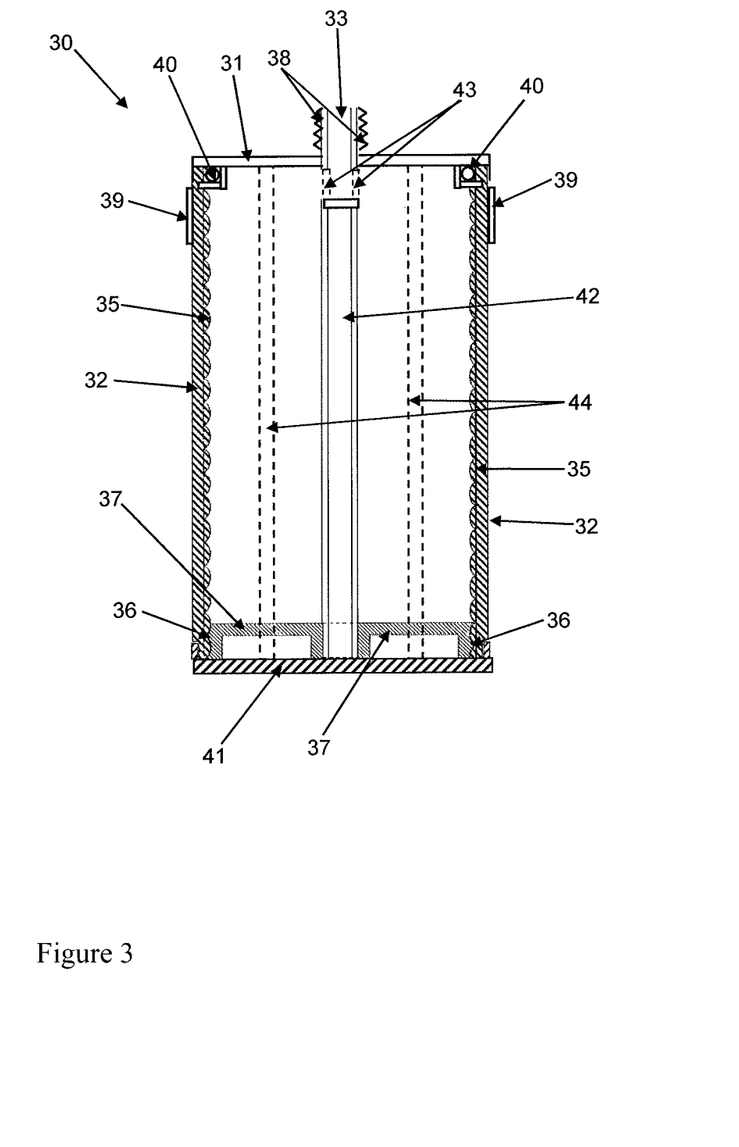
FIG. 3 is a schematic longitudinal sectional view through a container according to another embodiment of the invention.

FIG. 3 shows a schematic view of another container 30 according to the invention in a longitudinal sectional view. The container 30 comprises a circular cover 31 and a cylindrical container body 32 having circular cross section. In the cover 31 there is an outlet opening 33 in the form of a cylindrical tubular piece that extends through the cover 31. The cover 31 seals the one end of the container body 32.

On the inner side of the container body 32 there is provided a thread 35 in the form of an internal thread. A counter thread 36 in the form of an external thread, which is attached to a piston 37, engages in the thread 35 of the container body 32.

A fastener 38 in the form of an external thread is arranged on the tubular piece of the outlet opening 33. The fastener 38 here serves to fasten the entire container 30 to a discharge device (not shown). A peripheral rubber section 39 is provided on the outer side of the container body 32, by which the container body 32 can be rotated relative to the cover 31. For this purpose, the cover 31 is mounted so that it can rotate on the container body 32 with the help of a sealing bearing 40.

The end of the container body 32 opposite the cover 31 is closed by an end piece 41 that can be screwed on. In the axis of symmetry of the container body 32 there is a tube 42, which can be constructed with the tubular piece of the outlet opening 33. The tube 42 has openings 43 connected to the outlet opening 33 on the end facing the cover 31. The tube 42 is closed in the direction of the end piece 41, in order to prevent the penetration of the contents of the container 30 into the tube 42. The piston 37 includes an opening for the tube 42, so that the piston 37 can move along the tube 42 and the piston 37 seals tightly with the tube 42.

Two other rods 44 are arranged in the interior of the container 30 parallel to the longitudinal axis of the container body 32 and extend through openings in the piston 37. The piston 37 can move along the rods 44 in the longitudinal direction. The rods 44 ensure that the piston 37 cannot rotate in the container body 32, even with the cylindrical construction having a circular base surface of the container body 32. For this purpose, it would also be sufficient for the individual tube 42 arranged centrally to have a non-round shape, but instead, for example, a rectangular shape. On the side of the piston 37 facing the inner walls of the container body 32 there are provided seals, which should prevent the contents of the variable volume from being pressed out into the bottom part of the container 30 when a pressure builds up.

If the container 30 according to the invention is screwed with the fastener 38 into a discharge device, on which a roller is arranged that presses on the rubber section 39, then the container body 32 can be rotated relative to the outlet opening 33 and the cover 31 by rotating the roller. Since in this arrangement the piston 37 cannot rotate with the container body 32, because it is held in position by the rods 44 and optionally also by the tube 42, the piston 37 is moved in the direction of the cover 31 along the tube 42 and the rods 44 due to the force exerted by the thread 35 on the counter thread 36 of the piston 37. In this way, the contents of the container 30, for example a paste-like mass (not shown), which is contained in the variable volume located between the piston 37 and the cover 31, is pressed out from the outlet opening 33 into a discharge device. There it can be mixed, for example, with other materials, before it is applied on the target location. The propulsion of the piston 37 and thus the volume flow of the paste-like mass from the outlet opening 33 can be regulated by the rotational speed of the roller.

For all of the embodiments, like those according to FIGS. 1, 2, and 3, it is applicable that the outlet openings 13, 33 can be closed by closures and/or films, in order to prevent a penetration of foreign bodies or dirt into the container 10, 30.

Figure 4:
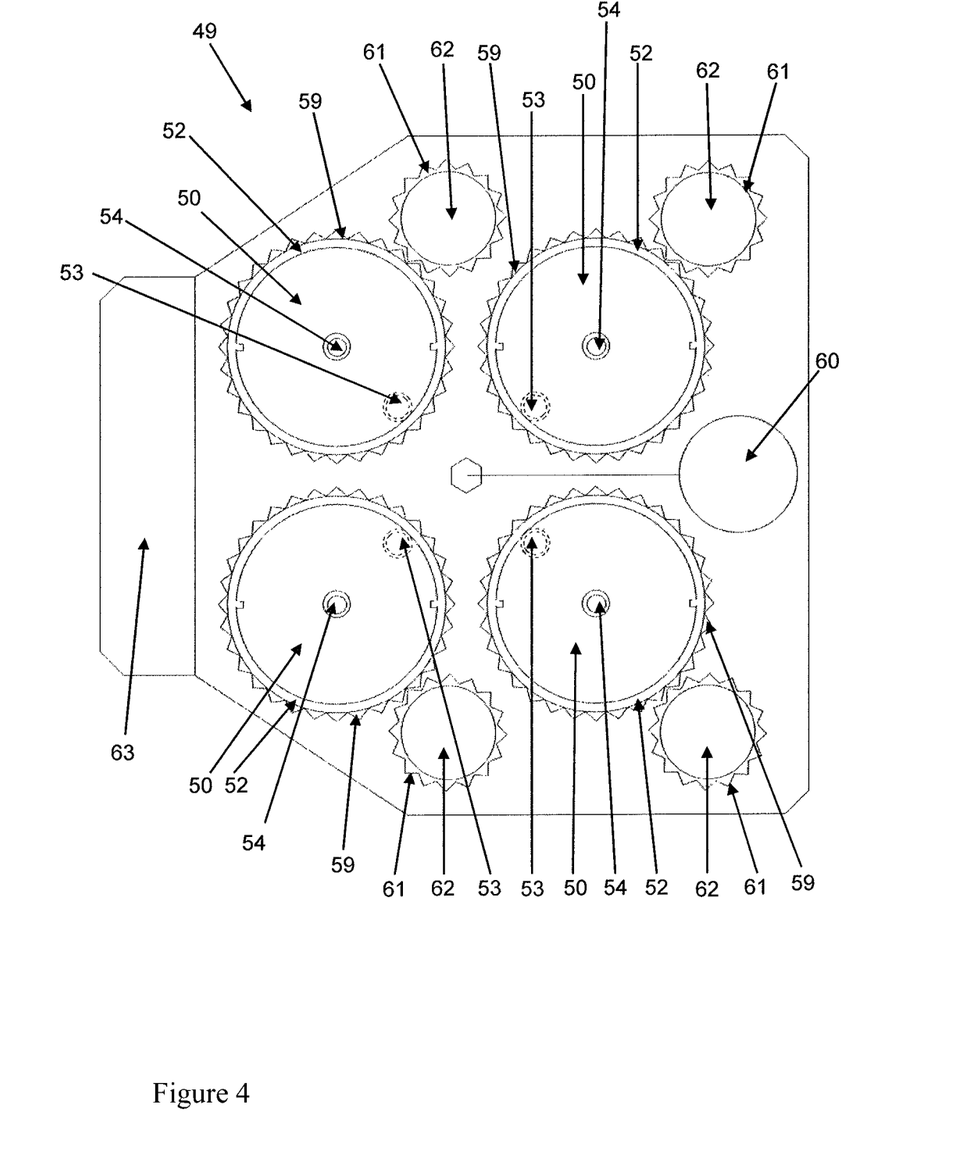
FIG. 4 is a schematic cross-sectional view of a container system according to an embodiment of the invention.

FIG. 4 shows a schematic cross-sectional view of a container system 49 according to the invention. Four containers 50, whose container body 52 walls are surrounded by ring gears 59, are part of the container system 49. Each container 50 comprises a spindle 54 or a tube 54 and an outlet opening 53, wherein the outlet openings 53 are connected to a mixer (not shown). The mixer is driven with a mixing shaft drive motor 60. A gear 61 that can be rotated by a cartridge drive motor 62 engages in the ring gear 59 of the container 50. In this way, any container body 52 of the container 50 can be rotated at different speeds and independently from each other by controlling the cartridge drive motors 62. The container system 49 can be set and controlled by a control element 63.

A certain mixing ratio of the contents of the different containers 50 and/or a certain volume flow of the mixed material can be set at the control element 63. It can also be possible by the control element 63 to set a desired consistency of the mixed material to be applied. From the desired consistency for known content of the container 50 or from the desired mixture ratio, a controller (not shown) calculates the rotational speed of the cartridge drive motors 62, which leads to a certain volume flow of the content from the individual containers 50 for a known propulsion of the pistons in the containers 50.

Here it is equivalent to set the gears that drive the ring gear 59 differently, in order to set the desired propulsion of the piston. In this case, optionally only one motor could also be used.

A mixing shaft drive motor 60 operates a mixing device, in which the original components from the containers 50 are mixed before being applied.

The user or a control unit of the container system 49 can recognize, with reference to the rotational speeds of the different containers 50, whether the setting desired by the user or control unit has been implemented. At the same time, it is easily possible to replace individual containers 50.

The features of the invention, disclosed in the preceding description and also in the claims, figures, and embodiments, can be essential both individually and also in any arbitrary combination for the implementation of the invention in its different constructions.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. A container for single-component or multi-component molding materials, the container comprising a container body having a constant outer contour in a longitudinal extent of the container, a piston movable in a direction of the longitudinal extent, and a cover having an outlet opening, wherein a variable volume for a molding material is defined between the piston and the cover in the direction of the longitudinal extent of, the container, wherein a thread is arranged in an interior of the container, the thread engaging in a counter thread of the piston and the piston being rotatably mounted relative to the thread, wherein the container body is rotatably mounted relative to the cover having the outlet opening and a rotation of the container body relative to the cover having the outlet opening leads to a rotation of the piston relative to the thread, such that the variable volume is varied and the content of the container is directly pressed out through the outlet opening, and wherein a ring gear is arranged peripherally around the container body to rotate the container body about the longitudinal extent thereof relative to the cover.

2. The container according to claim 1, wherein the cover is arranged on an end of the container opposite to an original position of the piston, wherein the original position of the piston is the position in which the variable volume is at a maximum.

3. The container according to claim 1, wherein the cover and/or the outlet opening is connected tightly to the container body.

4. The container according to claim 1, wherein the thread is an external thread arranged on a spindle in the interior of the container, which is fastened to or arranged on the cover.

5. The container according to claim 1, wherein the thread is constructed as an internal thread on an inner wall of the container body.

6. The container according to claim 1, wherein the container body has a cylindrical shape and the piston has a circular cross section, wherein the thread is arranged as an internal thread on an inner side of the container body and the counter thread is arranged as an external thread on an outer side of the piston and wherein the piston comprises an opening through which at least one rod and/or one tube extends in the longitudinal direction of the container, wherein this rod and/or tube is/are connected to the outlet opening and/or to the cover, such that the piston cannot rotate relative to the outlet opening.

7. The container according to claim 1, wherein a spindle comprising the thread as an external thread is arranged centrally in the interior of the container in the direction of the longitudinal extent, wherein the spindle is connected rigidly to the outlet opening and/or to the cover, and wherein the piston comprises a central opening having the counter thread as an internal thread, wherein the spindle extends through this opening, and wherein the piston is movable in the longitudinal direction relative to the container body but is not rotatably mounted relative to the container body and is tightly sealed with a inner wall of the container body.

8. A container system for multi-component molding materials, the container system comprising at least two containers according to claim 1, wherein one of the containers is provided for each component of the molding material, and the outlet openings and/or the covers of the containers are detachably connected to each other, and wherein the container bodies are rotatably mounted independently from each other.

9. The container system according to claim 8, wherein multiple drives are provided for multiple container bodies, wherein rotational speeds of the container bodies can be advanced and/or set independently from each other or in constant ratios, and a control element is provided for the input of parameters.

10. The container system of claim 8, wherein the outlet openings and/or the covers of the containers are pluggable into each other.

11. A method for applying a paste-like mass from a container according to claim 1, wherein the container body is rotated relative to the outlet opening, such that the piston is shifted by the thread in the direction of the cover and thereby presses a content of the container through the outlet opening.

12. A method for mixing multiple materials from containers of the container system according to claim 8, wherein and the rotational speeds of the container bodies are set depending on a desired mixing ratio.

\* \* \* \* \*